United States Patent [19]
Panetta

[11] Patent Number: 5,383,918
[45] Date of Patent: Jan. 24, 1995

[54] HYPOTHERMIA REDUCING BODY EXCLOSURE

[76] Inventor: Thomas F. Panetta, 4 Apple Tree La., Great Neck, N.Y. 11024

[21] Appl. No.: 938,828

[22] Filed: Aug. 31, 1992

[51] Int. Cl.⁶ .............................................. A61F 7/00
[52] U.S. Cl. ................... 607/104; 607/108; 607/112
[58] Field of Search ............................... 128/399–403; 607/96, 104, 108–112, 114

[56] References Cited

U.S. PATENT DOCUMENTS

| | | | |
|---|---|---|---|
| 26,663 | 1/1860 | French | 128/403 X |
| 695,496 | 3/1902 | Schermerhorn | |
| 1,489,046 | 4/1924 | Thompson | |
| 2,255,751 | 9/1941 | Bancel | 128/402 X |
| 3,085,405 | 4/1963 | Frantti | 128/402 X |
| 3,276,036 | 10/1966 | Cater | |
| 3,738,367 | 6/1973 | Hardy | 128/402 X |
| 3,849,802 | 11/1974 | Govaars | |
| 3,855,635 | 12/1974 | Ramirez | |
| 4,006,495 | 2/1977 | Jones | |
| 4,266,299 | 5/1981 | Beal | |
| 4,353,359 | 10/1982 | Milbauer | 128/402 X |
| 4,369,528 | 1/1983 | Vest et al. | |
| 4,370,757 | 2/1983 | Richmond | |
| 4,572,188 | 2/1986 | Augustine | |
| 4,759,083 | 7/1988 | Belcher | |
| 4,764,986 | 8/1988 | Stewart | |
| 4,765,323 | 8/1988 | Poettgen | |
| 4,930,161 | 6/1990 | Cohen | |
| 4,936,319 | 6/1990 | Neubardt | |
| 4,964,173 | 10/1990 | Gordon et al. | |
| 4,998,296 | 3/1991 | Stames | |
| 5,035,241 | 7/1991 | Walasek et al. | |
| 5,184,612 | 2/1993 | Augustine | |

Primary Examiner—Angela D. Sykes
Attorney, Agent, or Firm—Darby & Darby

[57] ABSTRACT

This invention is a heat conserving or cooling suit enclosure of plastic sheet for a patient undergoing a medical procedure or for a patient with hypothermia or hyperthermia from any cause. The enclosure is preferably compartmentalized to allow the sealing off of non-effected parts of the body to reduce or increase heat loss and if necessary, to actively heat or cool those parts while permitting full access to the areas which are the subject of a surgical procedure. The enclosure may have separate elements for the arms and legs with each of the compartments having a longitudinal preferably upstanding seam, readily openable to allow access to those areas for manipulation and procedures and which can be resealed around tubes and conduits inserted into or attached to the patient. The patient is placed upon each open component part of the enclosure while it is flat and the part is subsequently closed about the patient by engaging the longitudinal seams. The parts of the enclosure normally consist of head, arm, leg, abdominal and thoracic parts. Additional adhesive which directly contacts the patient is provided at the transverse areas bordering compartments which can be employed when one adjacent compartment is to be maintained in open condition to prevent heat loss from non-involved parts of the body of the patient. One or more portals for connecting air circulating, heating or cooling and dehumidifying devices to said enclosure can be attached as required.

11 Claims, 7 Drawing Sheets

HYPOTHERMIA REDUCING BODY EXCLOSURE

FIELD OF THE INVENTION

The present invention relates to the field of surgery and medicine and more particularly, to an improved enclosure for the body of a patient to reduce or increase the loss of body heat during the course of or because of a surgical procedure, trauma, sepsis, prolonged cold exposure, hyperthermia, malignant hyperthermia, or neonatal hypothermia. The present invention also relates to an improved method for heating such an enclosure.

BACKGROUND OF THE INVENTION

Hypothermia, which may be defined as body temperature below 36 degrees Celsius occurs for a variety of reasons during surgery. The ability of a patient to conserve heat and vary heat production during surgery and post operatively is disturbed by both anesthesia and exposure of the patient to the operating room environment. This loss of body heat occurs by conduction, evaporation, convection and radiation. Metabolic heat production by an anesthetized adult patient approximates 60–70K calories per hour. Conduction to the operating table and surgical drapes account for less than 10% of heat loss. Evaporation loss occurs from exhaled air and from exposed body cavities, and amounts to roughly 25K calories per hour. Variations in anesthesia circuitry including low flow systems, closed circuits, to and from systems and heat humidifiers can reduce evaporation losses to 10–15 calories per hour. Convection losses are naturally dependant upon ambient temperature. At 21 degrees Celsius the patient loses approximately 80 calories per hour which in itself is greater than the amount of heat the patient can produce over a like period. In addition, radiant heat loss is approximately 100 calories per hour.

Additional causes of hypothermia include cold exposure, major trauma, massive blood transfusions, sepsis in elderly patients, prolonged periods of unresponsiveness, maternal hypothermia and neonatal hypothermia in low birth weight infants.

Known methods used to reduce heat loss during and after a surgical procedure include heated and moisturized inhalation anesthetics, radiant heaters, warming blankets, reflecting blankets, increasing the temperature of intravenous infusions and blood transfusions and warm irrigation. It is also possible to increase ambient temperature, but this may cause operating personnel discomfort.

SUMMARY OF THE INVENTION

The present invention is an enclosure for the body of a patient undergoing a surgical procedure or a patient who develops hypothermia or hyperthermia for any reason. This enclosure effectively reduces heat loss because of radiation and convection, the greatest sources of loss. This enclosure can also be used for heat loss (cooling). This invention also includes a heating and cooling system for such an enclosure. As used hereinafter "heating system" encompasses both a system for cooling and/or heating air.

The enclosure is in the form of a suit that can be compartmentalized, transparent and adapted to enclose the arms, legs, thorax, abdomen, and in some cases the head of a human body. Each of these compartments can be individually opened and closed by means of a seam joined by a pressure sensitive adhesive or hook and loop fastener (e.g., Velcro—trademark of VELCRO TM USA, Inc., Manchester, N.H.). The seams facilitate the donning of the patient who often may be inert. The seams can be partially opened and resealed for the insertion of the patient or introduction of tubes, conduits or other equipment as needed. The seams preferably conform or mold to the shape and size of tubes and conduits and they may be further sealed, if needed, with pressure sensitive adhesive strips or tapes.

One or more compartments or areas can be opened to permit a surgical procedure. It is desirable to limit heat or cooling losses to such open areas. This is accomplished by providing separate adhesive seals on the inner surfaces of each compartment boundary which directly contact the patient to demarcate and seal air flow to and from that compartment. Compartments on either side of the surgical field can be connected to an external heating or cooling system for circulating and controlling heated or cooled air. Using known two piece compression grommets that can be attached to any location on the enclosure, tubing from an external air heating or cooling and circulating device and exhaust ports can be connected to one or more compartments. The portion of the enclosure encircled by the grommet can be cut away to access the compartments prior to connecting the tubing to the grommet. Other hose attachment fasteners can be used instead of two piece grommets including an adhesive connecting hose device.

A moisture absorbent material or desiccant can be incorporated in the suit, hoses, connecting device or temperature control unit, to retard the accumulation of moisture and/or the heating or cooling air can be dehumidified or dried. The body enclosure can be completely transparent to allow visualization of the entire body to permit continual inspection, monitoring and evaluation of the patient. Grounding plates can be built into the enclosure, especially at the end of an extremity compartment to allow grounding of one of more electrocautery devices or for other reasons. Sensors for monitoring the patient can be directly attached to or incorporated into the enclosure, for example a heat sensor to monitor the temperature of the enclosure or the temperature of the patient. These sensors can be used in a feedback loop to automatically control the heating or cooling system and the temperature of the enclosure or the patient.

In its broadest expression, this invention is an encasement for the body of a surgical patient for reducing or increasing heat loss and comprises a suit of a substantially gas impermeable flexible sheet material, sized to encompass the parts of a human body and having a longitudinally oriented separable seam substantially over the length of each part of the body.

Preferably the suit has an opening at one end allowing the head to extend therethrough and has arm elements. It may also have separate leg elements. The leg elements need not have seams but if there are arm elements it is preferred that they have longitudinal seams along the length thereof.

In a preferred embodiment, this invention is a body enclosure or suit having several compartments, each of which comprises a flexible sheet and has a re-openable seam for access to the compartment. The seams comprise pressure sensitive adhesive strips or hook and loop (VELCRO TM) fasteners along the length of the seam.

While the seam can be overlapping and lie flat, it is preferred that the fastening material be on the inner facing sides of the seam, such that when the two sides of the seams are joined, the seam is upstanding from the plane of the sheets. It is usually not necessary to have the seams absolutely airtight. The compartments of the enclosure can include head, arms, legs and abdominal/thoracic parts.

The body enclosure can have other pressure sensitive internal or external adhesive strips adjacent to compartment junctures adapted to seal the enclosure to the body to inhibit air flow to and from compartments. When an extremity compartment is removed, as for example, to operate on a thigh, or when a portion of a compartment is cut away for exposure of the surgical field, external pressured sensitive strips can be applied to seal the edges to maintain the circulation of heated or cooled air within the suit enclosure, and to prevent the heated or cooled air from circulating over the sterile surgical field.

The suit enclosure is preferably made of a substantially gas impermeable plastic sheet such as of polyethylene, polypropylene or PTFE. Sheet rubbers such as a neoprene can be used, as well as, plastic coated paper or cloth.

When the seams are upstanding as above described, a particular advantage of the present invention is that the parts of the enclosure can be cut from flat stock. The adhesive strips, if required for the seam are all on only one side and are applied before or after cutting of the sheets. Release strips are placed over the adhesive seams. The enclosure can then be folded and/or stacked flat for shipping and storage. Thus, only a minimal storage space is required for the stacked enclosures. Four sizes will usually be stocked: infant, small or young adult, regular adult and extra large adult, although additional sizes can be made as need be, alternatively an adjustable size can be used.

DRAWINGS

In the drawings, like, reference numeral designates like items throughout the several views, in which.

DESCRIPTION OF THE PREFERRED EMBODIMENT OF THE INVENTION

Figure 1:
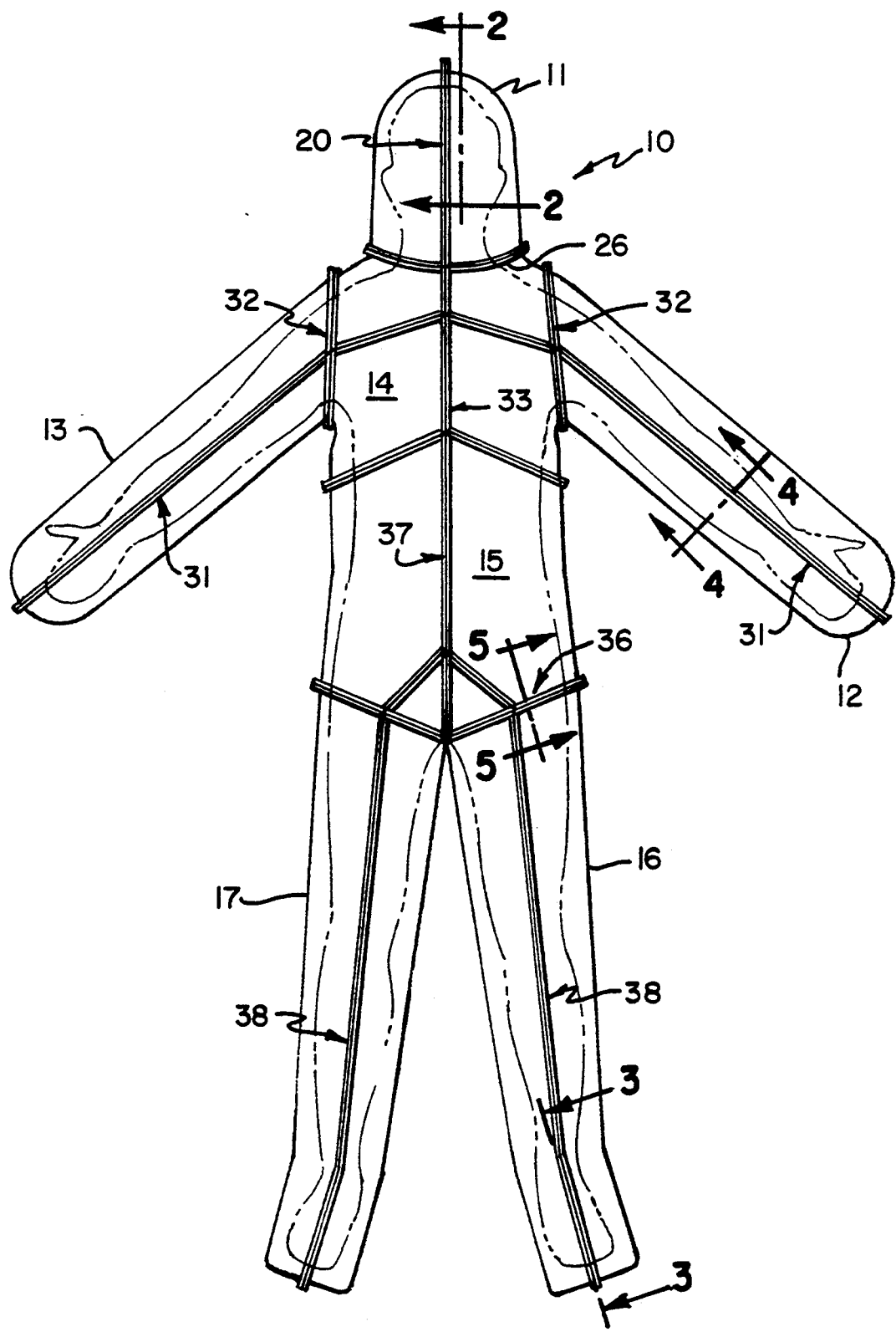
FIG. 1 is a front elevational view, somewhat schematic, of a suit enclosure according to this invention.

In accordance with the present invention an enclosure or suit, generally indicated by 10, is formed of a flexible plastic sheet such as a polyethylene or polypropylene sheet. Thickness of 0.05 to 1.0 mm are generally suitable although other thicknesses can be used. Where maximum transparency is not required, some or all of the components can be made from fibrous materials or a metalized plastic. The body enclosure includes a head element 11, left and right arm elements 12 and 13, respectively, thoracic/abdominal elements 14 and 15, respectively, and left and right leg elements 16 and 17, respectively.

Each element includes a longitudinal separable seam which enables the element to be placed about a part of the body of a patient and then resealed to encase that body part. For example, leg element 16 has longitudinal seam 38 and thoracic/abdominal elements 14 and 15, respectively, have longitudinal seams 33 and 37, respectively. These seams correspond to the seam 31 illustrated in FIG. 4. Each portion of the element 13A and 13B also can include an edge area having separable means 24, 23 respectively, for connecting with a corresponding area on an adjacent portion of an element whereby each element can be fully assembled. Similarly each element includes a transverse separable seam which enables adjacent elements to join together. For example, leg element 16 connects with abdominal element 15 at transverse seam 36 and arm element 13 connects to element 14 at transverse seam 32. All the transverse seams 26, 32, 35, and 36 are constructed in the same manner as the longitudinal seams 31, 33, 37 and 38. For example, the construction of transverse seam 36 of FIG. 5 corresponds to the construction of seam 31 of FIG. 4 except for the sealing strips discussed below. Referring now to FIG. 5, each element can additionally be provided adjacent its connecting edge area at transverse seams such as 35 and 36 with pressure sensitive adhesive strips 50, 53 for sealing to the body at that point. Such pressure sensitive strips 50, 53 are indicated next to the transverse seams 26, 32, 35 and 36 by dotted areas.

The pressure sensitive adhesive strips 50, 53 are protected by a release paper or the like 54, 55, respectively, in a known manner prior to use. It is preferable to have the pressure sensitive adhesive strip on both sides of a seam although it can be used on only one side or may not be used at all. Although contact adhesive strips can be used for the seams, it is preferable to use Velcro closures for the seams, particularly the major ones such as seams 33 and 37. Rather than have each of the elements 11, 12, 13, 14, 15, 16 and 17 supplied separately and then assembled on the patient, it is preferred to have the enclosure 10 supplied as a single, complete enclosure. To this end, all of the elements can be cut from flat strips as a single enclosure, or the elements such as 12 and 16 may be separately cut from a flat stock and then have the pressure sensitive and Velcro strips attached thereafter, or they can be permanently attached to the thoracic/abdominal unit 14 and 15 on the underside of the enclosure 10 as by a simple overlapping seam (not shown); this seam can be adhesively or heat welded in a known manner.

Depending on the particular design and considering the cost of waste material in some instances a more complete enclosure can be die cut from the plastic film. For example, head element 11 can be integrated and cut with the main body element 14 and 15, leaving just the arm and leg units to be attached.

Figure 2:
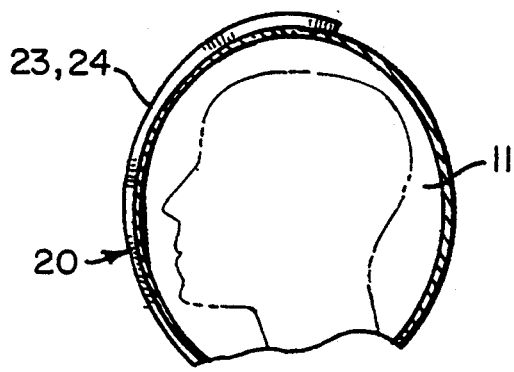
FIG. 2 is a fragmentary sectional view of the head element along the line 2—2 in FIG. 1.
Figure 3:
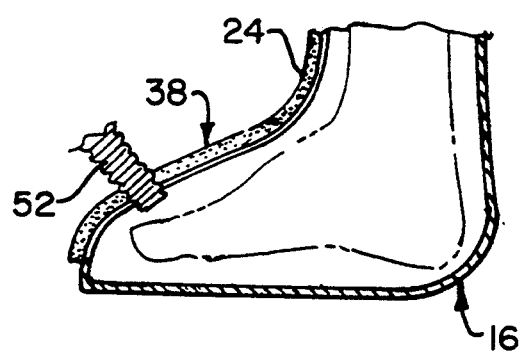
FIG. 3 is a fragmentary sectional view of a portion of a leg element along the line 3—3 in FIG. 1.
Figure 4:
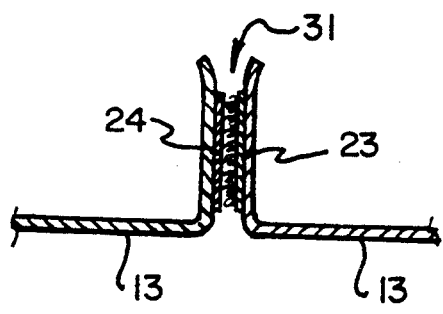
FIG. 4 is a fragmentary sectional view of a longitudinal oriented separable seam within one compartment along the line 4—4 in FIG. 1.
Figure 5:
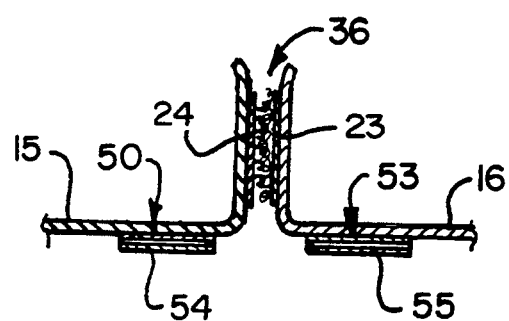
FIG. 5 is a transverse oriented seam joining one compartment to another along the line 5—5 in FIG. 1.

Referring to FIG. 2, the seam of head element 11 is shown in traverse view as 20, and this seam 20 is also constructed in the same manner as seam 31 illustrated in FIG. 4. The seam 31 consists of the two edges of the plastic sheets 13A and 13B each of which have in this case contact adhesive strips 23 and 24. These are turned upright as shown and brought into contact to make the seal.

Turning to FIG. 5, the element joining seams 36, having adhesive strips 23 and 24 attached to plastic sheets 10 and 16 and may be closed in a similar manner. These seams, in addition, have body contacting adhesive strips 50 and 53 on the underside as previously discussed.

Elements 16 and. 17 are symmetrical as are elements 12 and 13 so that only one die is needed for each pair.

When the patient has been positioned on the open body enclosure 10, the seams are joined by bringing the edges of the element up and around the patient and gently pressing them together. Of course, when pressure sensitive adhesive strips are used, the elements are joined one to another by bringing their edges together only after exposing the adhesive layer thereunder by removing its release paper. Also, if the underlying body-contacting strip is to be sealed to the patient, its release paper is removed prior to closing the seam.

Figure 8:
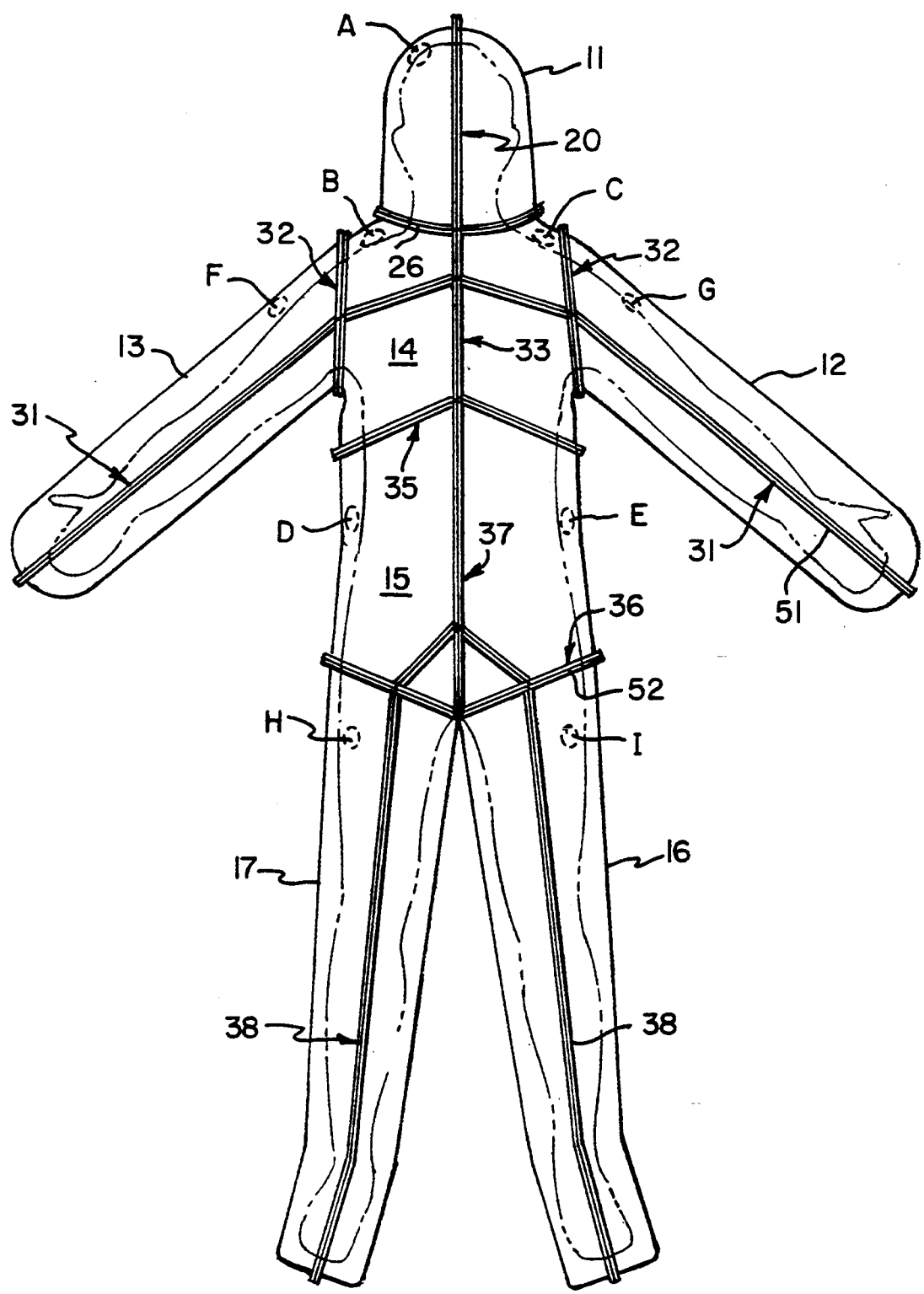
FIG. 8 is a front elevation view of the suit enclosure including air inlet portals according to the invention.
Figure 9:
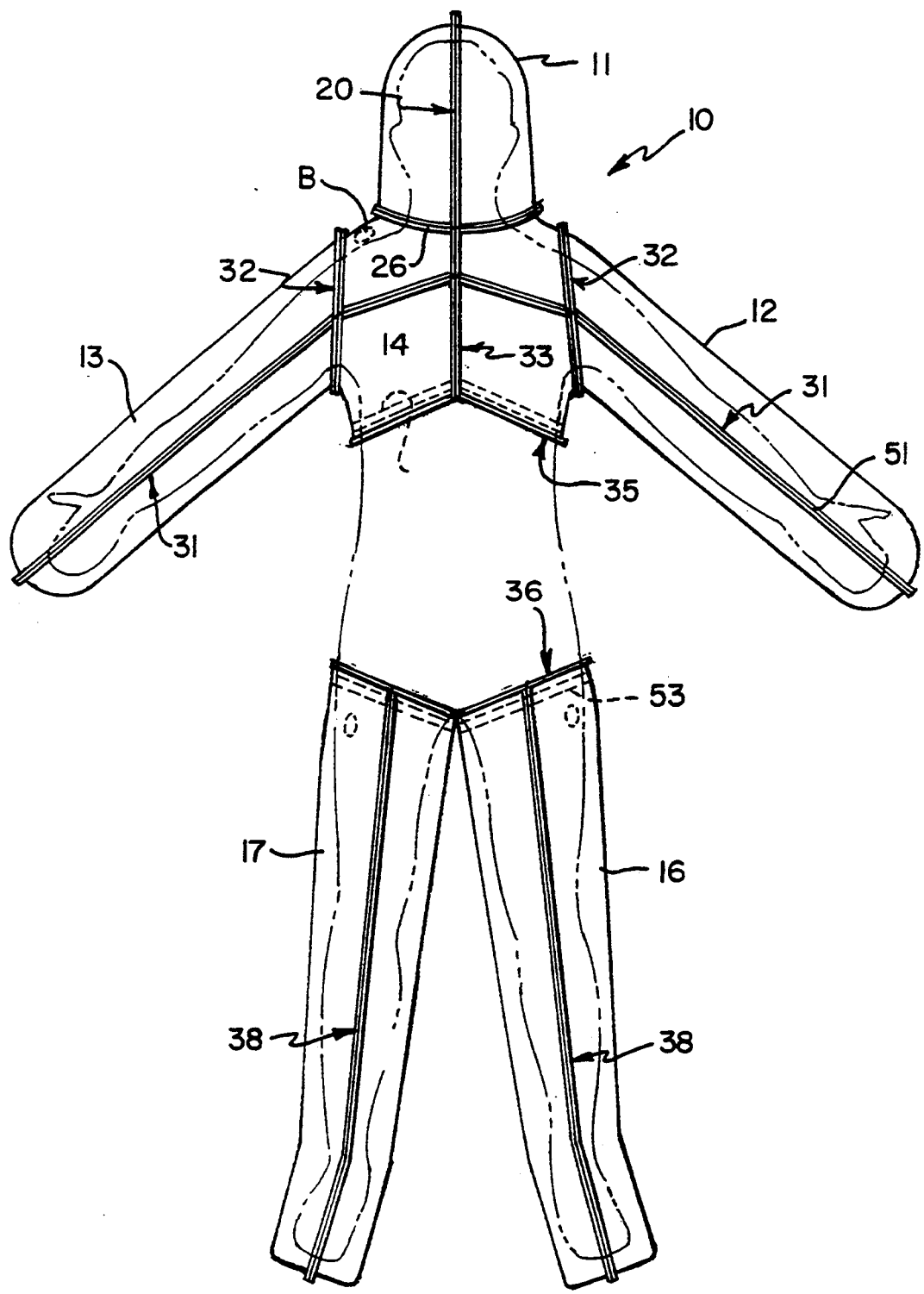
FIG. 9 is front elevation view of the suit enclosure set-up for performing an abdominal operation according to the invention.
Figure 10:
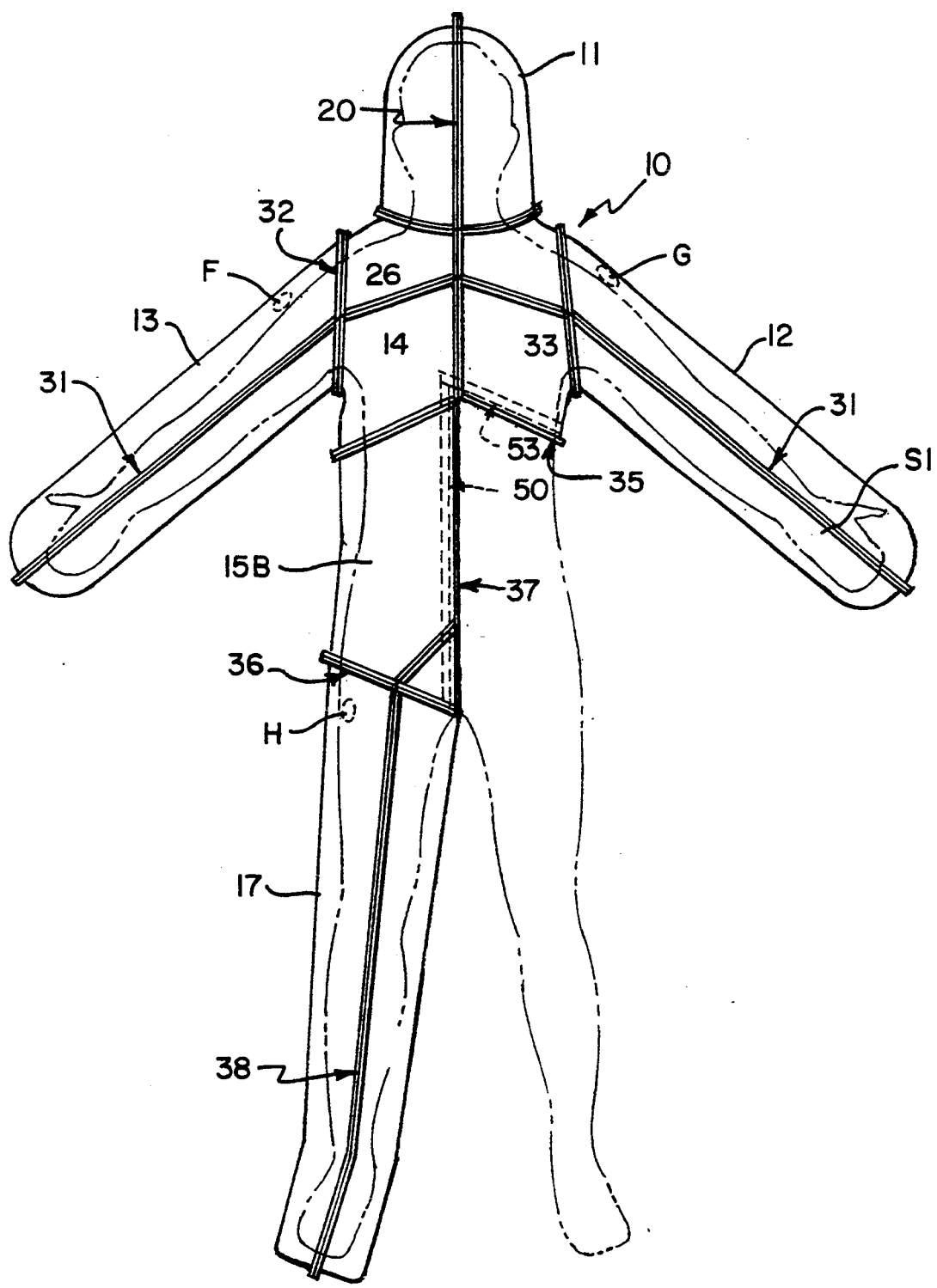
FIG. 10 is a front elevation view of the suit enclosure set up for performing a groin operation according to the invention.
Figure 11:
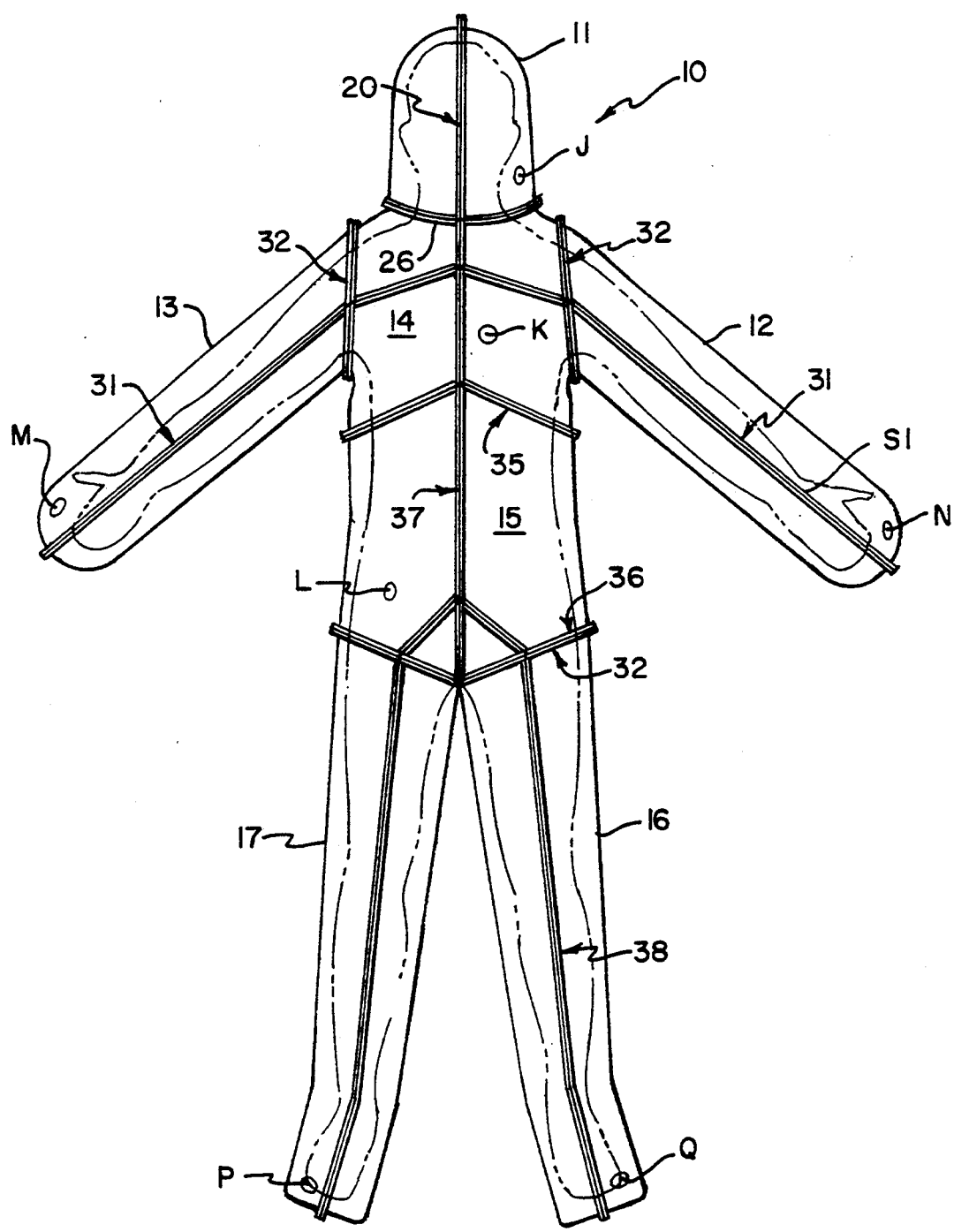
FIG. 11 is a front elevation view of the suit enclosure, including air exhaust portals according to the invention.

When it is desired to supply heated or cooled gas or air to the body enclosure 10, this is accomplished simply by closing a seam around an inlet tube 52 or as described in more detail infra. Such tube 52 can also be used as an outlet tube. Tube 52 could also be placed in one of the arm elements, leg elements, or other compartments as shown in FIG. 8. The gas is allowed to exhaust at any point therein by simply incorporating exit tubes at such point as shown in FIG. 11, or leaving the seam closed or partially open. Examples of the location of portals formed merely by closing a seam around an inlet/outlet tube 52 are portals S1 and S2 and are shown in FIGS. 8–11. In addition, the VELCRO ™ closures permit gas to escape. A more secure gas inlet/exit arrangement compared to simply closing the seam around an inlet tube is constructed of grommets (not shown) or utilize hose attachment devices as shown in FIG. 6 (and described in more detail infra) which can be attached to any area of the enclosure. Following the closure of a two piece grommet, the enclosure spanning the eyelet opening is cut away to open the portal thus allowing the air or gas supplied by inlet line 52 to pass into the enclosure 10. Similarly, exhaust ports can be attached at any point as shown in FIG. 10. It may be desirable to have one or multiple connections to an air/heating or cooling unit 100 as shown in FIG. 6 and described in detail infra, for the purposes of heating or cooling and dehumidifying, especially when suit compartments are isolated from one another by an intervening surgical field. Parameter sensors, such as, temperature and dehumidifying sensitive recording materials or sensors can be constructed within or on the outside of the suit enclosure as shown in FIG. 6 and described in more detail infra. The suit enclosure 10 can be constructed of a single layer of material or multiple layers with intervening air pockets for insulation and padding; e.g., the familiar air bubble type of insulation. While it is preferred that an element or compartment may be left off in order to expose the surgical field as shown in FIGS. 9 and 10 and described in detail infra, the plastic sheeting can also be cut away to expose the surgical field and the cut edges sealed to the body with an externally applied adhesive strip or tape, if a pre-existing seam is not available. Thoracic-/abdominal unit 14, and 15 can have a body contact adhesive strip 50 which can be used to seal against the patient if, for example, the thoracic or the abdominal area has to be exposed. These seams or external adhesives serve the purpose of sealing against the passage of air from each individual element or compartment not involved in the surgical procedure. Thus, the convection between areas enclosed by the individual elements is effectively prevented and heat or cooling losses will be confined to those areas which cannot otherwise be effectively sealed.

Two different types of air heating or cooling units can be utilized. The first is an air heating or cooling device that is used for compressed air lines that are available in operating rooms. In operating rooms without compressed air availability or in other areas of the hospital without compressed air availability (e.g. recovery rooms, intensive care units, emergency rooms), a free standing heating or cooling unit is used.

Figure 6A:
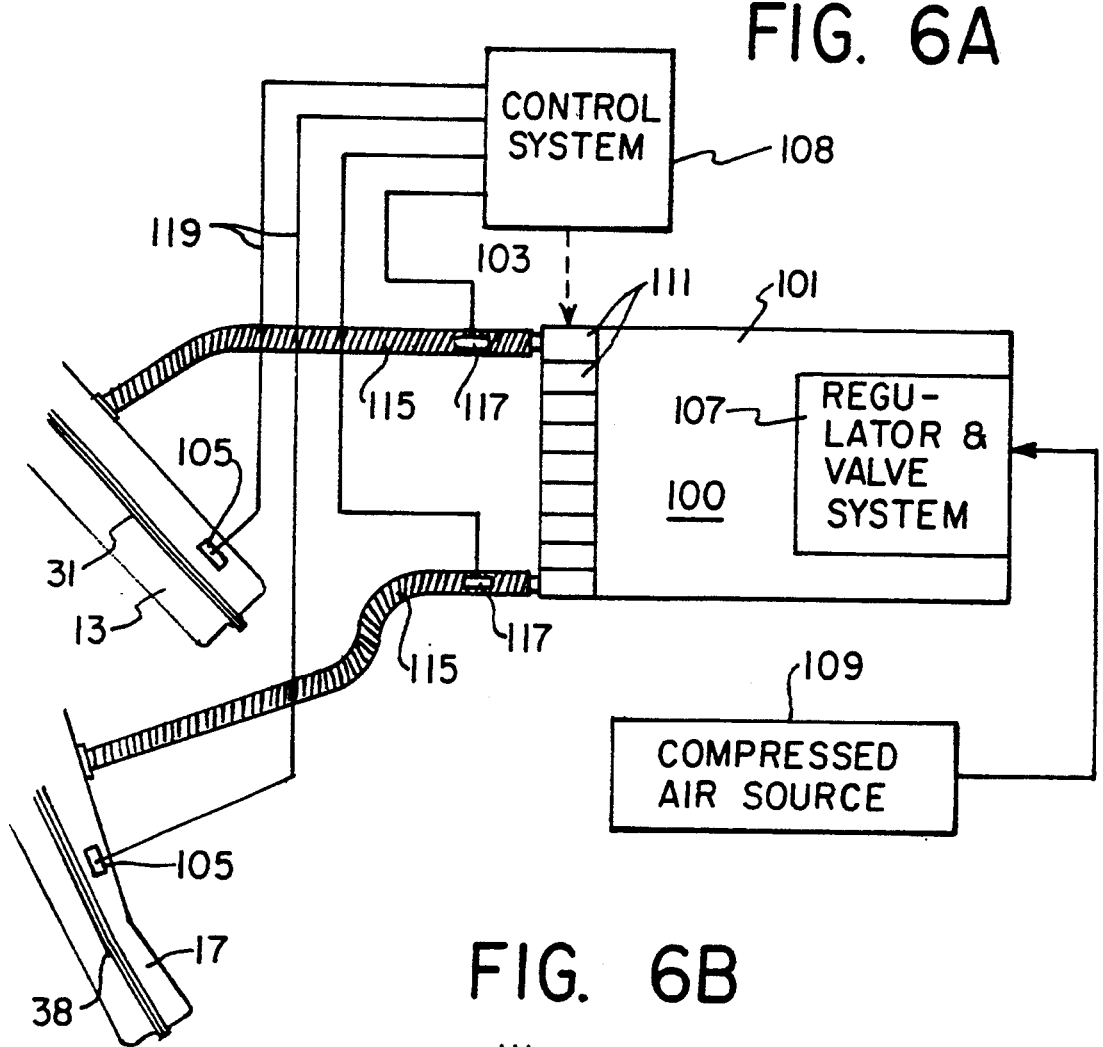
FIGS. 6A and 6B are functional block diagram of two types of air heating units shown attached to an arm and leg compartment of the suit enclosure of FIG. 1.

A heating or cooling unit for compressed air, generally designated by numeral 100, is illustrated in FIG. 6A. The unit 100 and comprises an electrically operated heater or cooler unit 101 with multi-ported heated or cooled air outlets 103 and parameter sensing means, or remote temperature sensing means, or sensors 105, on or within the suit 10 and/or on the patient (not shown) are used. The heating or cooling unit 101 contains a conventional regulator and valve system 107 that is attached in-line to a compressed air source 109. This system 107 provides for the control of air flow through the heater or cooler unit 101. The heater or cooler unit 101 has a conventional temperature control section or means 108 and conventional air flow control means 112 comprising individual, flow controls 111 for final output control of air flowing into multiple input portals (up to about nine) disposed on the suit 10 connected through tubing conduits 115 to the suit 10. The temperature control section 108 can include a plurality of separate temperature control units connected to the plurality of flow controls 111, so that the temperature of the air flowing through each of these units can be individually controlled, if desired. The final range of heat or cooling output (temperature and air flow) is modified depending on the volume of the particular compartment(s) being heated or cooled. An additional parameter sensing means or safety sensor(s) or temperature sensing means 117 is placed in the tubing conduits just downstream of the heating or cooling device 101. This safety sensor(s) 117 provides a signal to automatically regulate or cut off the heat or cool air generated to prevent overheating or overcooling of the patient.

The heating or cooling unit 101 can include two methods of controlling air flow and temperature. The first can be controlled automatically and utilizes a feedback loop 119 coupled to a conventional control system 121 which is coupled to the heating or cooling device 101 from remote sensor(s) 105. These remote sensor(s) 101 may be within the patient (e.g. internal rectal or esophageal thermosensors for determining core temperature), on the skin of the patient, and/or on or within the suit 10 as shown. The control system 121 is also used to automatically control the heating or cooling device 101 to prevent hypothermia or hyperthermia, respectively. The second method utilizes a manual control system 131 regulated by operating room personnel (anesthesiologists, nurses, surgeons). Both the manual and automatic systems include the downstream safety sensor(s) 117 which provides regulatory or cut off capabilities described supra.

Figure 6B:
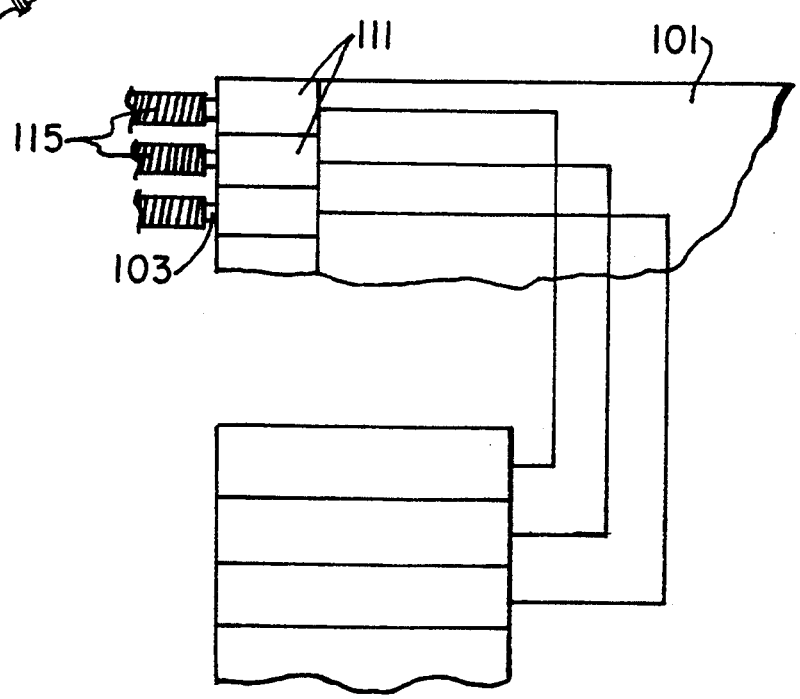

Referring now to FIG. 6B, the heating or cooling unit 101 can have multiple air outlet port capability so that from one to about nine tube conduits can be connected to heat or cool one or more compartments of the suit 10 at any given time. A conventional output port control system is incorporated in the heating or cooling device 101 to regulate the number of output ports that are functional at any given time. This port control may be as simple as individual on-off valves at each output connector, or as complex as independent regulatory devices to adjust the rate and volume of heated or cooled air flow delivered to an individual compartment of the suit 10 based on the individual volume and location of that compartment on the patient (i.e., heating or cooling the thorax or abdomen may have different requirements, than heating or cooling an arm or leg, based on body surface area to mass ratios).

The second type of air heating or cooling unit is a free standing heating or cooling unit that utilizes ambient air. All of the features described previously, except that the source of air will be ambient through an electrically operated air blower that has controls to adjust cubic feet per minute of air flow volume. As described previously the air flow can be controlled automatically through feedback from sensing devices, by manual controls or even utilize both methods.

Figure 7A:
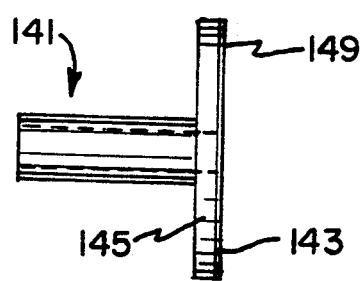
FIGS. 7A and 7B are side and perspective views of an adhesive connecting hose device adapted to connect to the elements of the suit enclosure of FIG. 1.
Figure 7B:
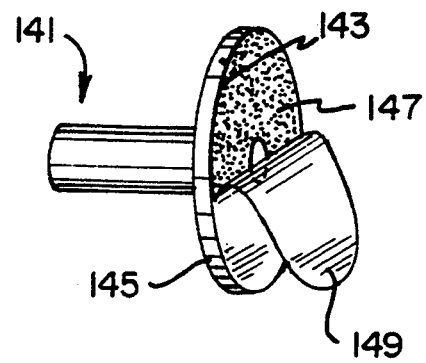

An alternative to the grommet system used as a hose attachment described previously is an adhesive connecting hose device 141 (FIG. 7). The flat lower surface 143 of the washer portion 145 of the connecting device 141 has an adhesive 147 affixed to surface 143 that is protected by a release paper 149. These adhesive connecting devices 141 are attached to different areas of the suit 10 depending on the type of operation performed. The central area of the suit surrounded by the washer portion 145 of the connecting device 141 are cut away or punched out after they are adhesively affixed to the upper surface of the suit 10, to allow airflow into the suit 10. The suit 10 also has partially perforated portals A through I on predetermined areas of the suit to facilitate attachment of the adhesive connecting devices 141, and "punching out" a hole therethrough for the entry of air. Such portals are shown in FIG. 8 and described in detail infra. Another alternative hose attachment means include a device that would punch out one or more of the partially perforated portals A-I and seal to the resulting hole(s) in the suit 10 at the same time (a "jack" type attachment). Each of these aforementioned hose attachment devices have a pressure sensitive fitting that inserts into one end of the hose, that is attached to the air heating units previously described.

Referring now to FIG. 8, the particular location of partially perforated air inlet portals A-I for hose connecting devices, used with such type of air inlet portals, are determined by the use of the suit 10 for standard or commonly performed operating (i.e., universal applications of the suit). However, in the case of an unusual application of the suit 10, hose attachments can be made to any area of the suit 10 that is required. These latter areas will not have the partially perforated portals described previously.

Referring again to FIG. 8, nine partially perforated inlet portals A-I are provided in the suit for conventional hose attachments. Portal A is located on the head compartment 11, portals B and C on the shoulder areas of the thoracic compartment 14, portals D and E on the anterolateral sides of the abdominal compartment 15, portals F and G on each of the arm compartments 12, 13, respectively, and portals H and I on each of the leg compartments 16, 17, respectively.

If for example, an abdominal operation is to be performed, there would be three areas of the suit 10 attached to three hoses from the heating or cooling unit (FIG. 9). Each leg compartment 16, 17 sealed to the patient at transverse seam 36, is independently attached to the heating unit at portals H and I, respectively. The upper portion of the suit 10, sealed to the patient at seam 35, may be attached to a single heater hose at portal B. This upper portion of the suit comprising the head, thoracic and arm compartments 11, 14, 12 and 13, respectively, may be heated as a single unit. Additional heater or cooler hoses can be attached to arm or head portals 12, 13, 11 respectively, to increase the heated or cooled air flow to this upper unit as needed.

If for example a groin operation is to be performed, one leg 17, and one-half of the abdominal portions 15B of the suit 10 would be removed (FIG. 10). The patient is then sealed to the suit 10 at seams 35 and 37. The remainder of the suit would be heated through portals F, G and H for operations resulting in mild degrees of hypothermia. Additional portals could be used for longer operations or situations predisposing to more severe hypothermia. The number of heating portals used would be an additional factor in regulating the amount of heat delivered to the patient.

In a situation predisposed to severe hypothermia with the additional problem of the need for a large surface area of the patient to be exposed to the operating field (e.g., an abdominal and lower extremity bypass requiring the abdomen and both legs to be in the operative field), only the head, arm and thoracic compartments 11, 12, 13, 14, respectively, would be available to deliver heated air to the patient. In this situation all five available ports A, B, C, F and G, would be utilized simultaneously. Since drapes used to cover the patient have substantial weight, the use of all such five portals may be necessary to increase the surface contact of heated air with the patient.

One possible anticipated finding may be that the suit 10 functions better by using all the portals available in every compartment, with or without separating the compartments by the adhesive strips 50, 53 attached to the patient.

Exhaust of air from the exhaust portals J-Q of the suit 10, as briefly described previously, can be simply accomplished by merely incorporating exit tubes or just leaving the VELCRO TM separating means 23, 24 partially open, or leaving the seam closed and allowing air to exit through the closed VELCRO TM seal. If adhesive is used to seal the longitudinal seams, then exhaust ports for the escape of air will be necessary. These exhaust ports, J-Q, like the input portals A-I, can be partially perforated portals located in areas of each compartment as shown in FIG. 11, such that they maximize airflow in contact with the patient's body surface.

The inlet portals A-I are preferably disposed on the suit 10, so as to use the shortest lengths of hoses, to increase conduction heating and cooling of the suit 10 thereby maximizing heating and cooling. The location of the portals also improves the efficiency and convenience of hose placement for operating room personnel.

Drying or desiccating agents such as calcium chloride can be incorporated within areas on the inner surface of the suit 10, within the tubing connecting the air heating or cooling unit to the inlet portals, on the air inlets to the air heating or cooling unit, or within the hose attachment devices. The hose attachment devices can likewise be attached at an exhaust portal to increase the drying capabilities of the suit. Drying or desiccating agents associated with the suit or hose attachment devices would also be discarded with the suit. Drying or desiccating agents associated with the heater can be compartmentalized to permit changing and refilling of these compartments with drying agents.

Normally, the head compartment will be left open and sealed to the neck with adhesive strips. Once the patient is anesthetized and with the anesthesia and monitoring equipment leads and tubes in place, the head compartment can then be closed about the surface of the communicating tubes. The suit enclosure 10 can, of course, be manufactured and sold without the head element, leaving the user to insulate or heat the head by other means.

During the course of a surgical procedure, convection loss will occur only from the compartments which are open for access to the surgical field. Radiation loss will be reduced depending upon the heat reflecting capability of the material from which the suit enclosure 10 is formed. In the case of metalized sheet material, the reduction of radiant heat loss may be greater than with clear plastic material. The plastic material can be lightly reflectively coated on the inner or outer surfaces so as not to unduly reduce transparency.

As previously noted, the device can be manufactured in a relatively small number of sizes; e.g. four, as close fitting is not required. It can be made and shipped flat with the adhesive strips thereon being only on one side and overlaid with a removable release sheet. The patient can be placed in the suit enclosure or removed from the enclosure by opening all the seams. Normally, the suit enclosure will not be reused as its low cost does not justify attempting to clean and reuse the suit enclosure.

The present invention may be embodied in other specific forms without departing from the spirit or essential attributes thereof and, accordingly, reference should be made to the appended claims, rather than to foregoing specification as indicating the scope of the invention.

What is claimed is:

1. A body enclosure having head, torso, arm and leg portions comprising:
   (a) a first sheet having a first end and a second end, said first sheet being made of a substantially gas impermeable flexible material;
   (b) means for releasably connecting said first end to said second end to form said enclosure fully about a body, said connecting means including a fastener and forming a longitudinally oriented seam with respect to said body;
   (c) a plurality of inlet port means for admitting fluid into said enclosure, said fluid being controlled to be within a predetermined temperature range, at least one of said inlet port means being disposed adjacent to the torso and at least another one of said inlet port means being disposed adjacent to one of said head, arm or leg portion;
   (d) a plurality of exhaust port means for discharging fluid from within said enclosure, at least one of said exhaust port means being disposed adjacent to said torso portion and at least another one of said exhaust port means being disposed through a passage located between the first end and the second end, said plurality of inlet port means and said exhaust port means cooperating with one another such that the flow of fluid within the enclosure permits a substantially even distribution of temperature controlled fluid therethrough to control the temperature of the body; and
   (e) said body enclosure comprising a plurality of removable sections to permit access to selected areas of the body during an operation, the remainder of the body enclosure, when a section is removed, being capable of being sealed to the body, so as to prevent the substantial leakage of the temperature controlled fluid and the disturbance of the even distribution of temperature controlled fluid within the enclosure.

2. The body enclosure as claimed in claim 1 wherein said plurality of inlet port means admits warm fluid into said enclosure.

3. The body enclosure as claimed in claim 1 wherein said plurality of inlet port means admits cool fluid into said enclosure.

4. The body enclosure as claimed in claim 1 wherein said longitudinal seam substantially encompasses said torso portion of said enclosure.

5. The body enclosure as claimed in claim 4 wherein said longitudinal seam substantially encompasses said head portion of said enclosure.

6. The body enclosure as claimed in claim 5 wherein said longitudinal seam substantially encompasses said at least one arm portion of said enclosure.

7. The body enclosure as claimed in claim 6 wherein said longitudinal seam substantially encompasses said at least one leg portion of said enclosure.

8. The body enclosure as claimed in claim 1 wherein said first sheet is made of a plastic material selected from the group consisting of polyvinylchloride, polyethylene, polypropylene and polytetrafluoroethylene.

9. The body enclosure as claimed in claim 1 wherein said plurality of inlet port means admits fluid from outside of said enclosure.

10. The body enclosure as claimed in claim 1 wherein said connecting means includes a hook and loop fastener.

11. The body enclosure as claimed in claim 10 wherein both said hook and loop fasteners are disposed on the same side of said first sheet such that when joined said longitudinal seam is perpendicular with respect to the surface of said body.

* * * * *